(12) United States Patent
Eden

(10) Patent No.: US 7,558,259 B2
(45) Date of Patent: Jul. 7, 2009

(54) SYSTEM AND METHOD FOR TRANSMITTING ANALYZED DATA ON A NETWORK

(75) Inventor: Gideon Eden, Ann Arbor, MI (US)

(73) Assignee: Centrus International, Inc., Ann Arbor, MI (US)

( * ) Notice: Subject to any disclaimer, the term of this patent is extended or adjusted under 35 U.S.C. 154(b) by 420 days.

(21) Appl. No.: 11/335,629

(22) Filed: Jan. 20, 2006

(65) Prior Publication Data

US 2006/0285539 A1    Dec. 21, 2006

(51) Int. Cl.
*H04L 12/50* (2006.01)
(52) U.S. Cl. ............... 370/378; 370/338; 713/201; 709/203; 709/224
(58) Field of Classification Search .......... 370/322, 370/338, 378; 709/224, 203; 713/201
See application file for complete search history.

(56) References Cited

U.S. PATENT DOCUMENTS

2004/0010720 A1* 1/2004 Singh et al. ............... 713/201
2004/0193449 A1* 9/2004 Wildman et al. ............ 705/2
2007/0282997 A1* 12/2007 Trochman .................. 709/224

* cited by examiner

*Primary Examiner*—Charles N Appiah
*Assistant Examiner*—Michael T Vu
(74) *Attorney, Agent, or Firm*—Ian C. McLeod

(57) ABSTRACT

An instrumentation network data system that transmits periodically measured instrument parameters or data to workstations residing on a computer network. A laboratory workstation residing on the network periodically collects and processes data from the instruments at predetermined collection time-intervals. The laboratory workstation includes a buffering data file to store the analyzed data. A supervisor workstation residing on the network periodically accesses the analyzed data from the buffering data file at predetermined supervision-time intervals and updates a supervision data file in the supervisor working station with the analyzed data. At predetermined viewing-time intervals, the supervisor working station can transmit the analyzed data to at least one viewing workstation residing on the network for remote viewing of the analyzed data.

43 Claims, 3 Drawing Sheets

SYSTEM AND METHOD FOR TRANSMITTING ANALYZED DATA ON A NETWORK

This application claims the benefit of priority of U.S. patent application Ser. No. 11/158,336, entitled "Instrumentation Network Data System," by Gideon Eden, filed Jun. 21, 2005, which is hereby incorporated by reference in its entirety.

TECHNICAL FIELD

The field of the invention pertains to the networking of one or more instruments, such as scientific or laboratory instruments, to a plurality of workstations also residing on a computer network. In particular, the invention pertains to periodic sampling of instrument parameters to update parameter values on an automatic basis with manual review by a laboratory operator as desired.

BACKGROUND

Typically, when monitoring laboratory instruments, the laboratory instrument is connected to computer, at which a user can view the results as they are processed. This requires the user to monitor the system to observe and report the results as they are processed. To communicate the processed results, the user typically must manually send the results over e-mail, or print out the results and hand deliver the results to a supervisor.

In situations where a sample is monitored in order to determine purity of a product to be distributed, it is critical to be able to expeditiously communicate the results of the monitored sample. Since a user monitoring the laboratory instrument and computer must take additional steps in providing the results to separate distribution centers and warehouses, there may be a significant delay in releasing a product for distribution and sale. Similarly, any delay in providing an indication that the representative samples are contaminated could result in a contaminated product being released into the distribution stream, potentially resulting in a subsequent product recall and/or product liability litigation.

Accordingly, a system able to monitor samples at a laboratory and transmit the results to remote and separate locations may facilitate the timely distribution of products, and prevent the distribution of samples not ready for release.

SUMMARY

Consistent with the present invention, there is provided a system for monitoring instrument data collected by an instrument comprising at least one laboratory workstation coupled to the instrument, and acquiring and analyzing instrument data; at least one viewer workstation coupled to a network; and at least one supervisor workstation coupled to the laboratory workstation and coupled to the viewer workstation through the network, the supervisor workstation acquiring the analyzed instrument data and selectively providing the analyzed instrument data to the viewer workstation.

Further consistent with the present invention, there is also provided a method of distributing instrument data to viewer workstations on a network, comprising acquiring instrument data at a laboratory workstation from an instrument; analyzing the acquired data; acquiring the analyzed data at a supervisor workstation; displaying the analyzed data at the supervisor workstation; and selectively transmitting the analyzed data to at least one viewer workstation.

Also consistent with the present invention, there is provided a system for monitoring instrument data collected by an instrument comprising at least one laboratory workstation coupled to the instrument, and acquiring and analyzing instrument data; at least one supervisor workstation coupled to the laboratory workstation the supervisor workstation acquiring the analyzed instrument data; and at least one viewer workstation coupled to the supervisor workstation through a network automatically accessing the analyzed instrument data from the supervisor workstation.

It is to be understood that both the foregoing general description and the following detailed description are exemplary and explanatory only and are not restrictive of the invention, as claimed.

The accompanying drawings, which are incorporated in and constitute a part of this specification, illustrates several embodiments of the invention and together with the description, serve to explain the principles of the invention.

DETAILED DESCRIPTION

Reference will now be made in detail to the present embodiments consistent with the invention, examples of which are illustrated in the accompanying drawings. Wherever possible, the same reference numbers will be used throughout the drawings to refer to the same or like parts.

Figure 1:
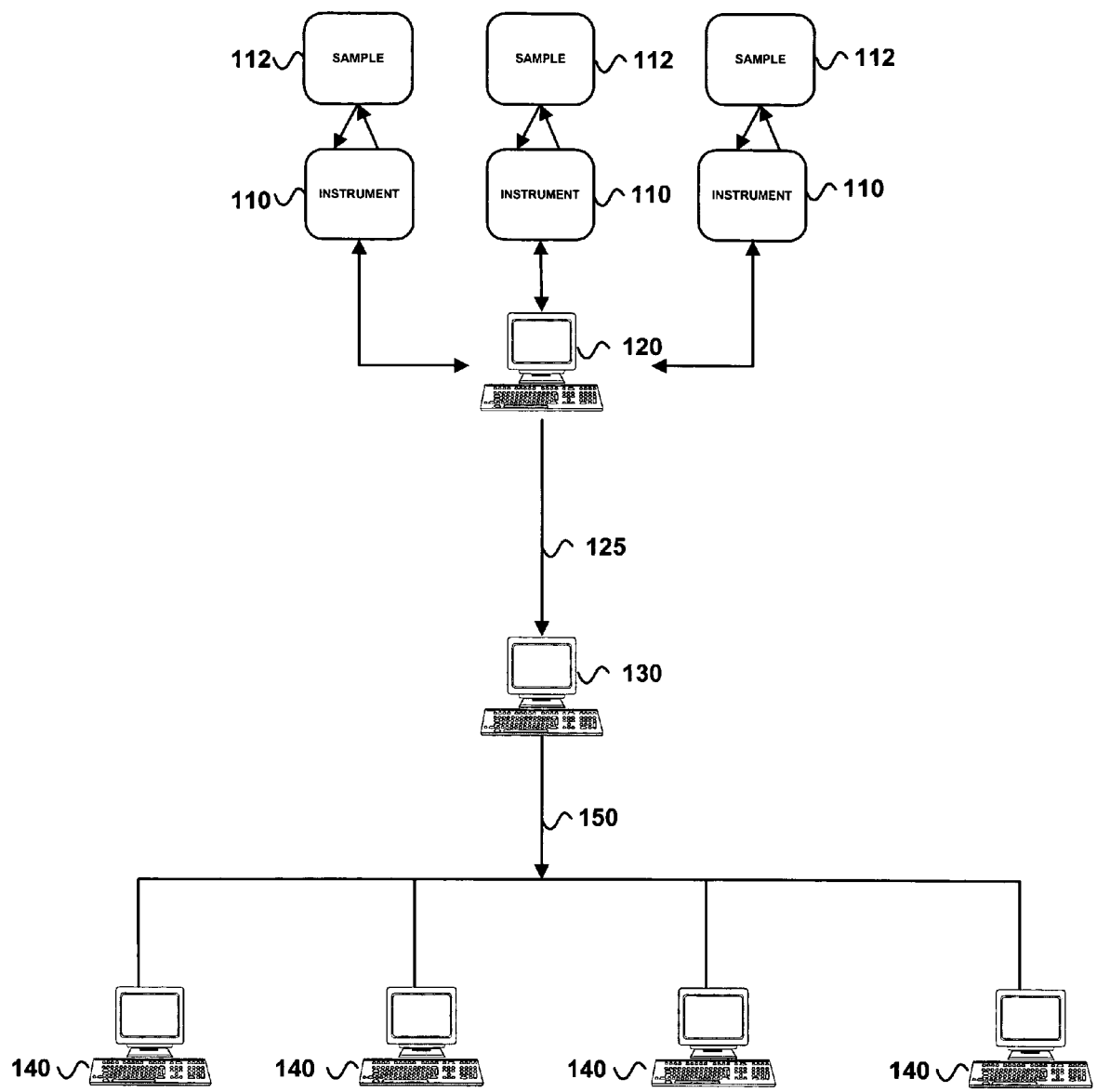
FIG. 1 illustrates an instrumentation network data system consistent with the present invention.

FIG. 1 illustrates an instrumentation network data system 100 consistent with the present invention. As shown in FIG. 1, an instrument 110 is connected to a laboratory workstation 120. Instrument 110 may be a typical laboratory instrument such as an incubator or contamination monitor, and may monitor a variety of properties of a sample 112, such as the concentration, purity, and/or contamination of the sample 112, and provide instrument data on the properties to laboratory workstation 120. In certain applications, instrument 110 may simultaneously monitor a plurality of samples. For example, instrument 110 may be a Soleris 32 or Soleris 128 incubator and monitoring system, commercially available from Centrus International, Inc.

Laboratory workstation 120 includes an input/output interface for communicating with the laboratory instrument and other workstations. Laboratory workstation 120 may also comprise software for analyzing data provided from instrument 110.

As shown in FIG. 1, laboratory workstation 120 is connected to a supervisor workstation 130 via a connection 125. Connection 125 may be of various types, such as a direct connection or a network. Supervisor workstation 130 is in turn connected to a plurality of viewer workstations 140 through a network 150. Network 150 may be of various types, such as, for example, a wide area network (WAN), a local area network (LAN) or an internet-based virtual personal network (VPN).

Workstations 120, 130, and 140 may be computers such as personal computers commercially available from the Hewlett Packard Corporation. Networks 125 and 150 may be operated according to protocols provided by networking software, such as provided in the Windows XP operating system commercially available from the Microsoft Corporation, or in Netware commercially available from Novell, Inc. In certain applications, networks 125 and 150 may operate according to different protocols provided by different network software.

Figure 2:
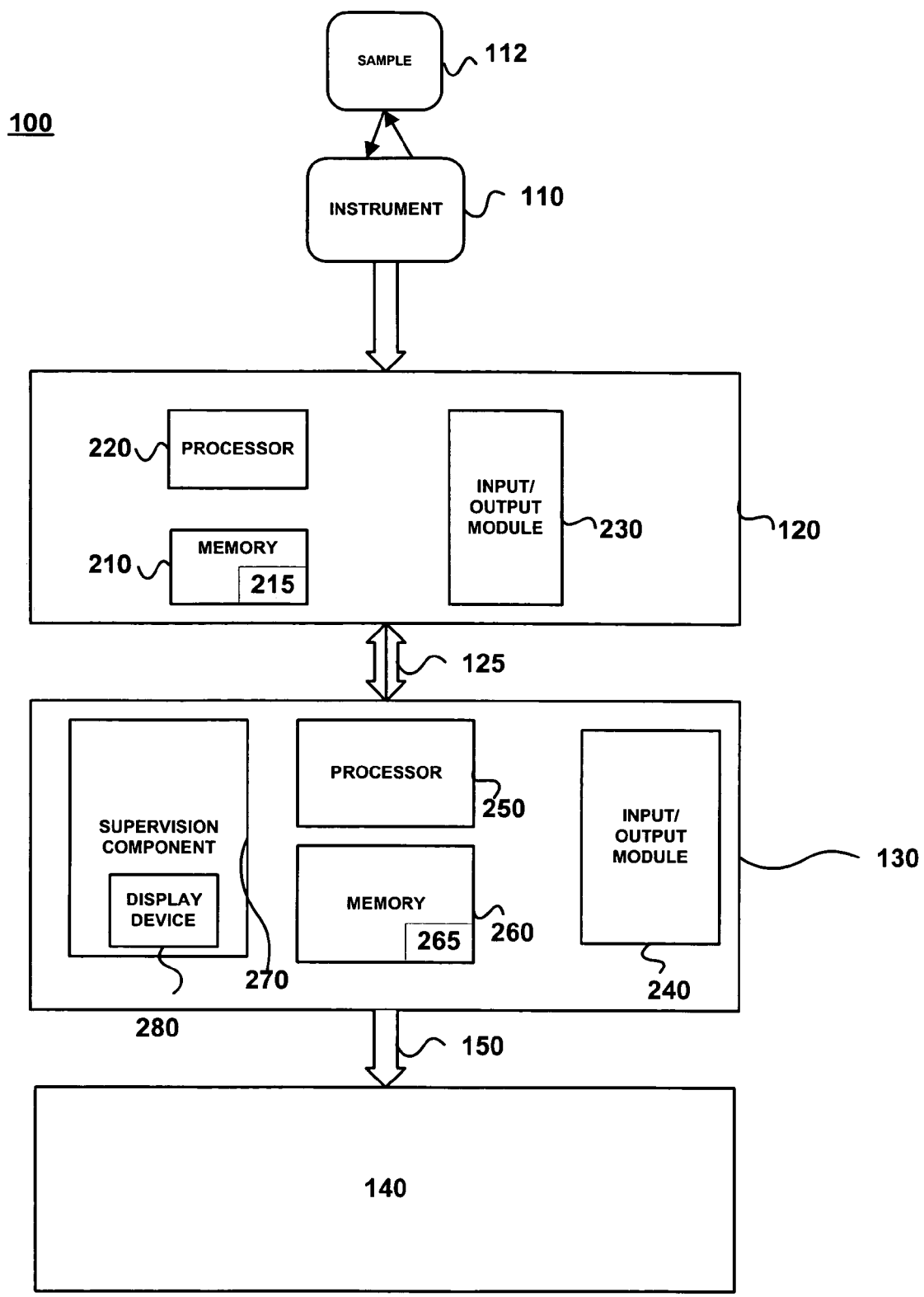
FIG. 2 illustrates the communication between components of the network of FIG. 1.

FIG. 2 illustrates the communication between instrument 110, laboratory workstation 120, supervisor workstation 130, and at least one of the viewer workstations 140.

Although only a single instrument 110 is shown in FIGS. 1 and 2, certain applications may employ a plurality of instruments 110 connected to a single laboratory workstation 120. Also, the systems illustrated in FIGS. 1 and 2 may employ a plurality of laboratory workstations 120 connected to a single supervisor workstation 130 and/or a plurality of supervisor workstations may be coupled to network 150.

As shown in FIG. 2, instrument 110 monitors sample 112 and acquires data. Laboratory workstation 120 periodically collects and analyzes data from the instruments, for example, at predetermined collection-time intervals. Laboratory workstation 120 includes instructions stored in a memory 210 for execution by a processor 220, the instructions including instructions for collecting and analyzing data from instrument 110, and for determining a collection-time interval. Memory 210 also includes data files, such as buffered data files 215, to store analyzed data output from processor 220 at or shortly after the collection-time intervals. Memory 210 may include a mass storage device such as a readable/writable disk, and/or may include a volatile or nonvolatile memory device, such as random access memory (RAM) or flash memory.

As shown in FIG. 2, processor 220 executes instructions stored in memory 210 for periodically collecting data from instrument 110 through an input/output module 230. Collected data is passed from input/output module 230 to memory 210. The data is then analyzed by processor 220 in accordance with instructions stored in memory 210. Data analysis may include determining if the data meets predetermined criteria, such as purity or contamination limits. Analyzed data is stored in buffered data files 215 in memory 210.

Laboratory workstation 120 communicates, via input/output module 230 over connection 125 with an input/output module 240 in a supervisor workstation 130. Supervisor workstation 130 also comprises a processor 250, and a memory 260. Memory 260 contains instructions to be executed by processor 250 to periodically access the analyzed data from the buffered data files 215 in memory 210 at, for example, predetermined supervision-time intervals. The analyzed data from the buffered data files 215 in memory 210 may be accessed either automatically, or in response to a user input, consistent with instructions in memory 260. Memory 260 may further contain instructions for determining the supervision-time intervals, and may further include a supervision data file 265, for storing the analyzed data acquired from laboratory workstation 120. Consistent with the present invention, collection-time intervals and the supervision-time intervals may be pre-configured or user-selected to be identical.

In operation, processor 250 executes instructions contained in memory 260 to periodically access the analyzed data from the buffered data files 215 in memory 210. The analyzed data may then be reviewed by a supervision component 270. Supervision component 270 comprises a display device 280 to display the analyzed data to enable a supervisor user to review and further analyze the data. Supervision component 270 may further comprise an automated reviewing system, wherein instructions in memory 260 are executed by processor 250 to automatically determine if the analyzed data satisfies predetermined criteria, also contained in memory 260.

After manual or automatic review, a status word residing in, for example, a buffered data file 215 in memory 210 is subsequently updated to indicate that the analyzed data has been reviewed.

After manual or automatic review, supervisor workstation 130 determines if the analyzed data should be transmitted to one or more viewer workstations 140. If so, processor 250 executes instructions contained in memory 260 to transmit the analyzed data from the buffered data files 215 in memory 210 to selected viewer workstations 140 through input/output module 230 and input/output module 240. The analyzed data or indications thereof may be transmitted to the viewer workstations 140 in response to a supervisor workstation 130 user's command, or it may be transmitted at predetermined viewing-time intervals. For example, the analyzed data or summaries thereof may be selectively transmitted to some viewer workstations 140 and not to others, in response to predetermined procedures set by instructions stored in memory 260 or in response to manual inputs received from a supervisor user. Consistent with the present invention, collection-time intervals, supervision-time intervals, and viewing-time intervals may be pre-configured or user-selected to be identical.

Alternatively, if memory 260 contains a supervision data file 265 storing the analyzed data, processor 250 may execute instructions contained in memory 260 to transmit the analyzed data stored in supervision data files 265, which is essentially a copy of the analyzed data stored in buffered data files 215, to selected viewer workstations 140 through input/output module 240. This may allow the direct transmittal of analyzed data to viewer workstations 140 without interrupting the collection and analysis of data by laboratory workstation 120.

System 100 may configure the viewing-time intervals to be equal to the collection-time intervals and/or the supervisor-time intervals, enabling near real-time transmission of the analyzed data between laboratory workstation 120, supervisor workstation 130, and at least one viewer workstation 140. System 100 may then display the analyzed data at viewer workstation 140.

System 100 may employ a records-locking scheme to avoid data access conflicts among the viewer workstations 140 receiving the buffered data files 215 or supervision data files 265.

In another embodiment consistent with the present invention, system 100 may be configured such that supervisor workstation 130 allows a predetermined at least one viewer workstation 140 to automatically access the analyzed data stored in supervision data file 265 for display on viewer workstation 140. In this embodiment, supervisor workstation 130 accesses analyzed data in buffered data file 215 of laboratory workstation 120, as described above, and stores the analyzed data in supervision data file 265. Memory 260 contains instructions to be executed by processor 250 which allows the automatic access of the analyzed data from the supervision data file 265 in memory 260 by one or more predetermined viewer workstations 140 at, for example, predetermined viewing-time intervals. As above, the predetermined viewing-time intervals may be pre-configured or user-selected to be identical to the collection-time intervals and the supervision-time intervals.

Alternatively, memory in one or more viewer workstations 140 may contain instructions to cause the viewer workstation 140 to automatically access the analyzed data in supervision workstation 120. Viewer workstation 140 may automatically gain access to the analyzed data over network 150 using protocols provided by networking software of the same type that operates network 125.

Figure 3:
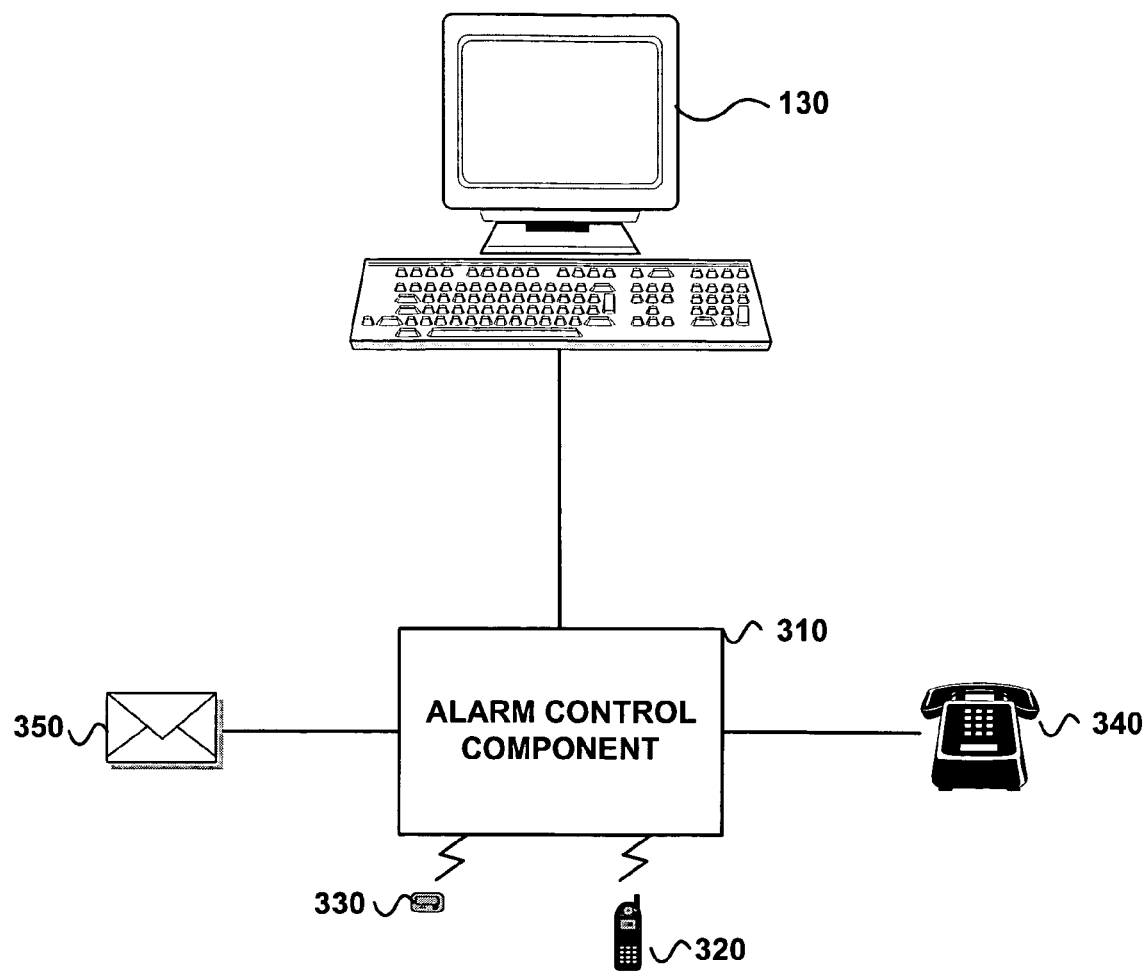
FIG. 3 is illustrates an alarm control component consistent with the present invention.

FIG. 3 illustrates an embodiment consistent with present invention, comprising an alarm control component 310 connected to supervisor workstation 130. Alarm control component 310 generates an alarm indication when analyzed data meets predetermined criteria. The alarm indicator may be audible, telephonic, or wireless in transmission, and may include wireless phones 320, pagers 330, traditional land-line phones 340, and email 350. For example, alarm control component 310 may comprise a system for generating an alarm, as discussed in copending U.S. application Ser. No. 11/183,761, entitled "Method and System for Generating a Telephone Alert Indicating the Presence of an Analyte," filed Jul. 19, 2005, by Gideon Eden.

Consistent with the present invention, alarm control component 310 may also be connected to at least one viewer workstation 140. Supervision component 270 may determine that the analyzed data does not meet predetermined criteria, and may transmit the alarm through input/output module 240 to at least one viewer workstation 140, to activate an alarm at the at least one viewer workstation 140.

Consistent with embodiments of the present invention, a sample 112 may be monitored at one location, and the analyzed data from the sample 112 may be selectively shared across network 150 to one or more viewer workstations 140 on network 150. System 100 may thus periodically provide analyzed data in essentially real-time to viewer workstations 140 on network 150, and may further provide an alarm when the data meets predetermined criteria. System 100 thus may aid in real-time decision making in determining when a product may be distributed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for monitoring instrument data collected by an instrument comprising: at least one laboratory workstation coupled to the instrument, and acquiring and analyzing instrument data from a sample; at least one viewer workstation coupled to a network; and at least one supervisor workstation coupled to the laboratory workstation and coupled to the viewer workstation through the network, the supervisor workstation acquiring the analyzed instrument data and selectively providing the analyzed instrument data to the viewer workstation; wherein: the laboratory workstation acquires and analyzes the data at predetermined collection-time intervals; the supervisor workstation acquires the analyzed instrument data at predetermined supervision-time intervals; and the supervisor workstation provides the analyzed instrument data to the viewer workstation at predetermined viewing-time intervals.

2. The system of claim 1, wherein: the collection-time intervals, the supervision-time intervals, and the viewing-time intervals are identical.

3. The system of claim 1, wherein the supervisor workstation comprises: supervision means for determining whether the analyzed data meets predetermined criteria.

4. The system of claim 3, wherein the supervision means further comprises: display means for displaying the analyzed data at the supervisor workstation.

5. The system of claim 4, wherein: the viewer workstation comprises a display component for displaying the analyzed data at the viewer workstation.

6. The system of claim 3, wherein the laboratory workstation comprises: an input/output module for communicating on the network; a first memory, containing instructions; a processor, for analyzing the instrument data in accordance with the instructions; data files in the first memory, the analyzed instrument data being stored in the data files; and a status word in the first memory, the status word updated after a review of the analyzed instrument data.

7. The system of claim 6, wherein: the supervisor workstation comprises an input/output module for selectively transmitting the data files to the viewer workstation.

8. The system of claim 6, wherein: the supervisor workstation comprises an input/output module for selectively transmitting the supervision data files to the viewer workstation.

9. The system of claim 4, wherein the supervision means further comprises: an automatic reviewing system for automatically determining if the analyzed data meets predetermined criteria.

10. The system of claim 3, further comprising: alarm control means for providing an alarm indication when the analyzed data meets predetermined criteria.

11. The system of claim 10, wherein: the alarm control means is connected to the supervisor workstation.

12. The system of claim 10, wherein: the alarm control means is connected to the viewer workstation.

13. The system of claim 10, wherein the alarm indication comprises: at least one of an audible, telephonic, or wireless alarm.

14. The system of claim 10, wherein the alarm indication comprises: at least one of an alarm transmitted via telephone, wireless phone, pager, or e-mail.

15. The system of claim 1, wherein the supervisor workstation comprises: an input/output module for communicating on the network; a second memory, containing instructions; a processor; and supervision data files in the second memory, for receiving analyzed instrument data.

16. The system of claim 1, wherein the network comprises: at least one of a local area network (LAN), a wide area network (WAN), or a virtual personal network (VPN).

17. The system of claim 1 wherein concentration, purity or contamination of a sample is monitored.

18. A method of distributing instrument data to viewer workstations on a network, comprising: acquiring instrument data from a sample at a laboratory workstation from an instrument; analyzing the acquired data; acquiring the analyzed data at a supervisor workstation; displaying the analyzed data at the supervisor workstation; and selectively transmitting the analyzed data to at least one viewer workstation; wherein: the laboratory workstation acquires and analyzes the data at predetermined collection-time intervals; the supervisor workstation acquires the analyzed instrument data at predetermined supervision-time intervals; and the supervisor workstation provides the analyzed instrument data to the viewer workstation at predetermined viewing-time intervals.

19. The method of claim 18, wherein: monitoring an instrument comprises monitoring an instrument at predetermined collection-time intervals; acquiring the analyzed data comprises acquiring the analyzed data at predetermined supervision-time intervals; and transmitting the analyzed data comprises transmitting the analyzed data at predetermined viewing-time intervals.

20. The method of claim 19, wherein: the collection-time intervals, the supervision-time intervals, and the viewing-time intervals are identical.

21. The method of claim 18, wherein the network comprises: at least one of a local area network (LAN), a wide area network (WAN), or a virtual private network (VPN).

22. The method of claim 18, wherein reviewing the analyzed data comprises: determining if the analyzed data satisfies predetermined criteria.

23. The method of claim 22, comprising: generating an alarm when the analyzed data fails to satisfy predetermined conditions.

24. The method of claim 23, wherein the alarm comprises: at least one of a wireless, telephonic, audible, or e-mail alarm.

25. The method of claim 18, wherein analyzing the data comprises: storing the data in buffered data files.

26. The method of claim 18, wherein displaying the analyzed data comprises: displaying the analyzed data on a display means for manual review.

27. The method of claim 26, comprising: updating a status word in a memory device of the laboratory workstation to indicate that the analyzed data has been displayed.

28. The method of claim 18, comprising: executing instructions contained in a memory of the supervisor workstation to automatically review the analyzed data.

29. The method of claim 18, wherein transmitting the analyzed data comprises: employing a records-locking scheme on the analyzed data to avoid data access conflicts.

30. The method of claim 18, wherein transmitting the analyzed data comprises: displaying the analyzed data at the viewer workstation.

31. A system for monitoring instrument data collected by an instrument comprising: at least one laboratory workstation coupled to the instrument, and acquiring and analyzing instrument data from a sample; at least one supervisor workstation coupled to the laboratory workstation via a first network, the supervisor workstation acquiring the analyzed instrument data and selectively providing the analyzed instrument data to a second network, the first network using first network protocols; and at least one viewer workstation coupled to the supervisor workstation through the second network, the viewer workstation automatically gaining access to the analyzed instrument data at the supervisor workstation over the second network using second network protocols; wherein: the laboratory workstation acquires and analyzes the data at predetermined collection-time intervals; the supervisor workstation acquires the analyzed instrument data at predetermined supervision-time intervals; and the supervisor workstation provides the analyzed instrument data to the viewer workstation at predetermined viewing-time intervals.

32. The system of claim 31, wherein: the second network protocols are identical to the first network protocols.

33. The system of claim 31, wherein: the at least one viewer workstation automatically accesses the analyzed instrument data at predetermined intervals.

34. The system of claim 31, wherein: the laboratory workstation acquires and analyzes the data at predetermined collection-time intervals; the supervisor workstation acquires the analyzed instrument data at predetermined supervision-time intervals; and the viewer workstation automatically accesses the analyzed instrument data from the supervisor workstation at predetermined viewing-time intervals.

35. The system of claim 34, wherein: the collection-time intervals, the supervision-time intervals, and the viewing-time intervals are identical.

36. A system for monitoring instrument data collected by an instrument comprising: at least one laboratory workstation coupled to the instrument, and acquiring and analyzing instrument data from a sample; at least one viewer workstation coupled to a network; and at least one supervisor workstation coupled to the laboratory workstation and coupled to the viewer workstation through the network, the supervisor workstation acquiring the analyzed instrument data and selectively providing the analyzed instrument data to the viewer workstation; and wherein the supervisor workstation comprises: supervision means for determining whether the analyzed data meets predetermined criteria; wherein: the laboratory workstation acquires and analyzes the data at predetermined collection-time intervals; the supervisor workstation acquires the analyzed instrument data at predetermined supervision-time intervals; and the supervisor workstation provides the analyzed instrument data to the viewer workstation at predetermined viewing-time intervals.

37. The system of claim 36, wherein the supervision means further comprises: display means for displaying the analyzed data at the supervisor workstation.

38. The system of claim 37, wherein the supervision means further comprises: an automatic reviewing system for automatically determining if the analyzed data meets predetermined criteria.

39. The system of claim 36, wherein the laboratory workstation comprises: an input/output module for communicating on the network; a first memory, containing instructions; a processor, for analyzing the instrument data in accordance with the instructions; data files in the first memory, the analyzed instrument data being stored in the data files; and a status word in the first memory, the status word updated after a review of the analyzed instrument data.

40. The system of claim 36, further comprising: alarm control means for providing an alarm indication when the analyzed data meets predetermined criteria.

41. The system of claim 40, wherein: the alarm control means is connected to the supervisor workstation.

42. The system of claim 40, wherein: the alarm control means is connected to the viewer workstation.

43. A system for monitoring instrument data collected by an instrument comprising: at least one laboratory workstation coupled to the instrument, and acquiring and analyzing instrument data from a sample; at least one viewer workstation coupled to a network; and at least one supervisor workstation coupled to the laboratory workstation and coupled to the viewer workstation through the network, the supervisor workstation acquiring the analyzed instrument data and selectively providing the analyzed instrument data to the viewer workstation; wherein the instrument is adapted to monitor at least one property of the sample selected from the group consisting of concentration, purity, contamination and combinations thereof and the instrument is selected from the group consisting of an incubator, a contamination monitor and combinations thereof; wherein: the laboratory workstation acquires and analyzes the data at predetermined collection-time intervals; the supervisor workstation acquires the analyzed instrument data at predetermined supervision-time intervals; and the supervisor workstation provides the analyzed instrument data to the viewer workstation at predetermined viewing-time intervals.

* * * * *